United States Patent
Watkins et al.

[11] Patent Number: 5,874,105
[45] Date of Patent: *Feb. 23, 1999

[54] LIPID VESICLES FORMED WITH ALKYLAMMONIUM FATTY ACID SALTS

[75] Inventors: David C. Watkins, Port Jefferson Station; Thomas J. Vichroski, Bayport; James A. Hayward, Stony Brook, all of N.Y.

[73] Assignee: Collaborative Laboratories, Inc., East Setauket, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 594,175

[22] Filed: Jan. 31, 1996

[51] Int. Cl.⁶ .................................................. A61K 9/127
[52] U.S. Cl. ............................. 424/450; 264/4.1; 264/4.3
[58] Field of Search ........................... 424/450; 436/829; 935/54; 264/4.1, 4.3

[56] References Cited

U.S. PATENT DOCUMENTS

| | | |
|---|---|---|
| 2,650,165 | 8/1953 | Wahl . |
| 3,957,971 | 5/1976 | Oleniacz ................................... 424/70 |
| 4,016,100 | 4/1977 | Suzuki et al. ........................... 252/316 |
| 4,032,663 | 6/1977 | Kobayashi et al. . |
| 4,217,344 | 8/1980 | Vanlerberghe et al. . |
| 4,235,871 | 11/1980 | Papahadjopoulos et al. . |
| 4,247,411 | 1/1981 | Vanlerberghe et al. . |
| 4,342,826 | 8/1982 | Cole . |
| 4,483,921 | 11/1984 | Cole . |
| 4,485,054 | 11/1984 | Mezei et al. . |
| 4,533,254 | 8/1985 | Cook et al. . |
| 4,619,794 | 10/1986 | Hauser . |
| 4,663,167 | 5/1987 | Lopez-Berestein et al. . |
| 4,708,861 | 11/1987 | Popescu et al. . |
| 4,721,612 | 1/1988 | Janoff et al. . |
| 4,761,288 | 8/1988 | Mezei . |
| 4,812,312 | 3/1989 | Lopez-Berestein et al. . |
| 4,857,319 | 8/1989 | Crowe et al. . |
| 4,873,088 | 10/1989 | Mayhew et al. . |
| 4,888,288 | 12/1989 | Wagner . |
| 4,897,269 | 1/1990 | Mezei . |
| 4,908,154 | 3/1990 | Cook et al. . |
| 4,911,928 | 3/1990 | Wallach . |
| 4,978,654 | 12/1990 | Lopez-Berestein et al. . |
| 5,000,958 | 3/1991 | Fountain et al. . |
| 5,032,457 | 7/1991 | Wallach . |
| 5,128,139 | 7/1992 | Brown et al. . |
| 5,164,182 | 11/1992 | Meybeck et al. . |
| 5,190,764 | 3/1993 | Chiba et al. . |
| 5,262,310 | 11/1993 | Karube et al. . |
| 5,277,913 | 1/1994 | Thompson et al. . |
| 5,296,231 | 3/1994 | Yarosh . |
| 5,366,881 | 11/1994 | Singh et al. . |
| 5,443,839 | 8/1995 | Meybeck . |
| 5,466,467 | 11/1995 | Singh . |
| 5,494,803 | 2/1996 | Carbonell ................................ 435/7.92 |
| 5,585,109 | 12/1996 | Hayward et al. . |

FOREIGN PATENT DOCUMENTS

| | | |
|---|---|---|
| 0 158 441 A2 | 10/1985 | European Pat. Off. . |
| 0158441 | 10/1985 | European Pat. Off. . |
| 0 561 424 B1 | 3/1997 | European Pat. Off. . |
| 57-82311 | 11/1980 | Japan . |
| 0082311 | 5/1982 | Japan . |

OTHER PUBLICATIONS

Hargreaves, W.R. et al., *Monoalkyl Liposomes* 17(18):3759, 1978.
Kaler, E.W. et al., *Science* 245:1371, Sep. 22, 1989.

*Primary Examiner*—Gollamudi S. Kishore
*Attorney, Agent, or Firm*—Darby & Darby

[57] ABSTRACT

A liposome for use in encapsulating both hydrophobic and hydrophilic substances (i.e., a "payload"), is disclosed which is capable of delivering their load upon the occurrence of a trigger or control condition. The liposomes are formed to stably encapsulate a particular active agent to form a delivery vehicle for the agent. The liposomes of the delivery vehicle are stable in a particular environment but become unstable or permeable if passed from the stable environment (e.g., characteristic of a particular pH and/or temperature and/or ionic strength) to a changed or unstable environment, thereby delivering their payload.

25 Claims, 5 Drawing Sheets

LIPID VESICLES FORMED WITH ALKYLAMMONIUM FATTY ACID SALTS

BACKGROUND OF THE INVENTION

The present invention relates to the production of lipid vesicles (liposomes) and, more particularly, to the production of liposomes from long chain alkylammonium fatty acid salts.

Liposome formation is a natural result of the amphipathic nature of the molecules of which they are comprised. Amphipathic molecules are those molecules with distinct regions of the molecule having hydrophilic character and distinct regions of the same molecule having hydrophobic character. When dispersed in water, amphipathic molecules form three types of macro-molecular structure: micelles, hexagonal phase and lipid bilayers. The exact macromolecular structure which is formed depends on the relative sizes of the hydrophilic and hydrophobic regions of the molecule.

Micelle formation is favored when the cross sectional area of the hydrophilic region of the molecule is greater than that of the hydrophobic part of the molecule. Detergents are examples of such molecules, e.g., sodium palmitate. Detergents contain a hydrocarbon chain (the hydrophobic portion of the molecule) and an ionic base (the hydrophilic portion of the molecule), and act as emulsifying agents to bind water and oil phases. That is, detergents allow oil and water to be broken into tiny droplets suspended or dispersed in water. Particular detergents 1 may be classified as anions (negatively charged at the hydrophilic portion) and may be represented, as shown in FIG. 1, as having a hydrophilic head 2 with a hydrocarbon (hydrophobic) tail 4. FIG. 2 is a representation of a micelle structure 5 formed of a number of detergent molecules due to their hydrophilic/hydrophobic character.

In the opposite conformation, i.e., when the cross sectional area of the hydrophobic region of the molecule is greater than that of the hydrophilic part of the molecule, the formation of hexagonal phase structures is favored, e.g., dimyristoylphosphatidylethanolamine (DMPE). FIG. 4A is a representation of a hexagonal phase structure, sometimes referred to as an inverse micelle.

For molecules in which the cross sectional area of the hydrophilic region of the molecule is slightly less than, or equal to, that of the hydrophobic part of the molecule, such as many phospholipids, the formation of bilayers is favored, e.g., dipalmitoylphosphatidylcholine (DPPC). Phospholipids are an amphipathic type of lipid which contain phosphate, that is, molecules containing one phosphate, a glycerol and one or more fatty acids. FIG. 3 is a simplified representation of a phospholipid molecule 6, including a hydrophilic head 8 (i.e., the phosphate and glycerol) and a hydrophobic tail 10 (i.e., the one or more fatty acids). FIG. 4 is a representation of a phospholipid bilayer 12, where the hydrophobic regions 14 of the phospholipid molecules are caused to turn inward due to the aqueous environment, and the hydrophilic portions 16 face outward. These bilayers are two dimensional sheets in which all of the hydrophobic portions, e.g., acyl side chains, are shielded from interaction with water except those at the ends of the sheet. An energetically unfavorable interaction of the acyl chains with water results in the folding of the bilayers to form three-dimensional, vesicles. These vesicles are referred to as "liposomes".

Liposomes may be formed as a single bilayer enclosing a single aqueous space (small unilamellar vesicles; SUVs) or may be composed of concentric bilayers with many aqueous spaces alternating with the bilayers (multilamellar vesicles; MLVs). Liposomes can be used to encapsulate both hydrophobic and hydrophilic materials. Hydrophobic payloads are typically partitioned within the bilayers whereas hydrophilic payloads are typically trapped within the aqueous compartments. The advantages of using liposomes as a carrier/encapsulation system is that they are stable and can protect their payload from degradation, e.g., by oxygen, digestive enzymes, etc.

For example, U.S. Pat. No. 3,957,971, issued May 15, 1976, discloses liposome-formed moisturizing units which are capable of moisturizing and improving flexibility, plasticity, and softness of keratinous matter, particularly mammalian skin. The liposomes within which the moisturizer is stored include a matrix of a ternary lipid mixture of lecithin, dicetyl phosphate, and a sterol, and include cavities disposed within the liposome. The cavities (lamellar space) contain an humectant, such as sodium pyroglutamate, in an aqueous medium. Moisturizing liposomes are also disclosed therein which function osmotically, serving as traps for water, which may be shared with the keratin constituents as required.

Liposomes also may be used for the timed delivery of a wide variety of materials including pharmaceuticals, cosmetics and nutrients. For example, U.S. Pat. No. 4,016,100, issued Apr. 5, 1977, discloses a method of producing a pharmaceutical composition comprised of an aqueous suspension of an active agent entrapped in a spherule of a phospholipid (liposome) The composition, or drug delivery vehicle, is prepared by dispersing a phospholipid uniformly in water to give an aqueous phospholipid dispersion, adding a medicament to the aqueous dispersion and freezing the thus-obtained aqueous dispersion to entrap the medicament in lipid spherules formed. The frozen dispersion is then thawed to realize an aqueous suspension of spherules having diameters of less than 5.0 microns. The timed release of an active agent is directly related to the amount of active agent trapped in the liposomes. The greater the amount of active agent, the longer the release process lasts.

A goal of the liposome research has been the development of a liposomal delivery system that would deliver its payload not over time as in the '100 patent mentioned above, but on cue, i.e., a controlled release, for example, in a mammalian body. For example, a delivery system that delivers its payload when applied to the skin or when arriving at a tumor. A bulk of the research has been based on admixtures of liposomes and other biological macromolecules such as antibodies and lecithins. Various degrees of success have been achieved with these systems but none have produced a liposome that will release its payload, or not, depending on the prevailing conditions. The invention described herein is just such a liposome: the degree of payload encapsulation may be altered by changes in pH and/or ionic strength of the surrounding medium thereby realizing a triggered delivery system in a form of a liposome.

OBJECTS AND SUMMARY OF THE INVENTION

It is therefore an object of the present invention to provide a lipid vesicle, or liposome, and method for manufacturing same, which overcomes the limitations of the prior art.

It is another object of the present invention to provide a liposome and method for manufacturing same which includes a controlled load delivery ability.

It is another object of the present invention to provide a liposome that is formed with an acyl $N_n$, $N_n$-dimethyl-1 diamino alkyl (ADDA) molecule, and method for manufacturing same.

It is another object of the present invention to provide a liposome which delivers its entrapped load at the occurrence of a preset condition, and method for inexpensively manufacturing same.

It is another object of the present invention to provide a liposome which displays cationic characteristics, and method for manufacturing same.

It is another object of the present invention to provide a liposome formed with alkylammonium fatty acid salts, e.g., trialkylammonium fatty acid salts, of long chain amides such that a portion of the molecular structure defined thereby includes a portion which readily adheres to protein and like molecules, and method for manufacturing same.

In one preferred embodiment, the present invention discloses a composition of matter, i.e., liposomes, for use in encapsulating both hydrophobic and hydrophilic substances (i.e., a "load"). The liposomes formed accordingly are capable of delivering their loads upon the occurrence of a trigger or control condition. For example, a liposome of this invention may stably encapsulate an active agent, genetic material or personal care element. Upon being passed from an environment characteristic of a particular pH or temperature, their molecular structure becomes unstable in the changed environment causing the liposomes to deliver their load. Such a composition of matter, i.e., liposome, may be formed in accordance with the process or processes of manufacture disclosed herein. Such liposomes are marketed under the tradename CATEZOMES™.

CATEZOMES™ liposomes are prepared as follows: a fatty acid of between 12 and 28 carbon atoms is linked via an amide bond to a primary amino group of an $N_n$, $N_n$-dimethyl-1, n-diamino alkyl (DDA) chain, where n can be in a range of about 2 to 10. The fatty acid, e.g., behenic acid, is then linked to the DDA chain. The neutralized material formed thereby is an acyl $N_n$, $N_n$-dimethyl-1, n-diamino alkyl (ADDA) chain. The ADDA chain is then mixed with a fatty acid of between around 10 to 32 carbon atoms in equimolar proportions and at a pH of between around 5 to 11 such that a salt bond is formed between a quaternary amine group of the ADDA and a carboxyl group of the fatty acid. The result is an acyl ADDA (A-ADDA) salt. The salt bridge and the process of facilitating the same is key to the products formed thereby. The A-ADDA molecule formed is polar in the salt bond region, but typically carries a net charge of zero (zwitterionic). The alkyl chain region of the molecule is hydrophobic. By altering the ratio of fatty acid to ADDA, the net surface charge of the liposomes described hereby can be made anionic, cationic or neutral.

Preferably, the A-ADDA molecules are dispersed in water or any suitable buffering solution having a pH of around 5 to 11 and an ionic strength of less than about 1 molar NaCl. Dispersion is perfected either by using a mechanical homogenizer at ambient temperature or by stirring at a temperature above that of the melting point of the components of the mixture. Following the dispersion of the hydrocarbons in the buffer system, the mixture is subjected to high-sheer processing. Hydrophobic interactions between acyl chains form the A-ADDA molecules such that they take on a shape which is approximately cylindrical in cross section. The A-ADDA molecules, therefore, form bilayers, and liposomes, in aqueous solution. Accordingly, the stability of the liposomes is dependent upon the pH (changing) and/or ionic strength of solution. By decreasing the ratio of the Acyl:ADDA, a liposome which displays a cationic nature at the hydrophilic portion of the molecule is formed, i.e., CATEZOMES™ liposomes, which display powerful and useful binding abilities to proteins and like materials.

DETAILED DESCRIPTION OF THE PRESENT INVENTION

Figure 1:
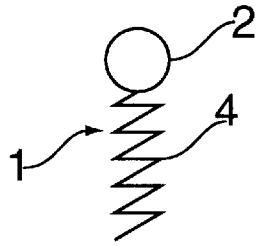
FIG. 1 is a pictorial representation of a detergent molecule.
Figure 2:
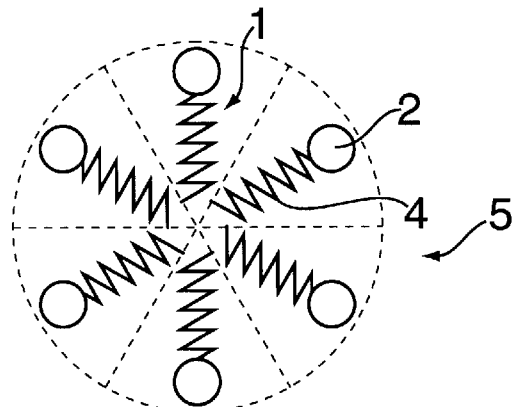
FIG. 2 is a pictorial representation of a micelle structure formed of a detergent molecule such as that represented in FIG. 1.
Figure 3:
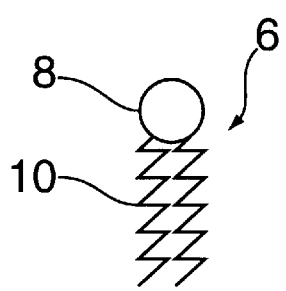
FIG. 3 is a pictorial representation of a phospholipid molecule.
Figure 4:
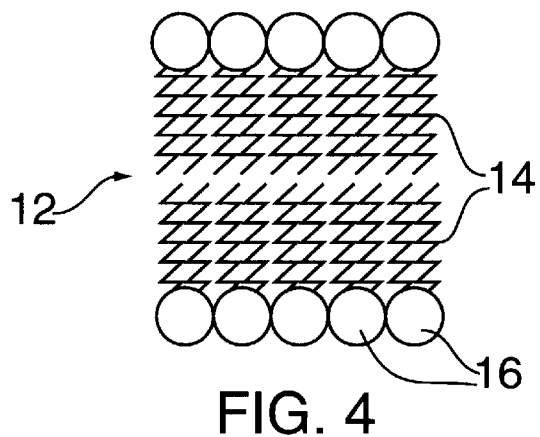
FIG. 4 is a pictorial representation of a phospholipid bylayer.
Figure 4A:
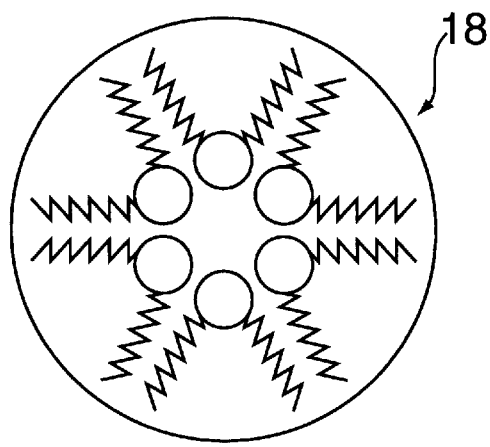
FIG. 4A is a pictorial representation of a converted micelle.

This invention relates to water-insoluble lipid vesicles prepared from alkylammonium fatty acid salts. While liposomes are not new, liposomes which can be inexpensively and efficiently formed and which display cationic characteristics as well as an ability to deliver their loads at the occurrence of a predetermined triggering condition are heretofore unknown. For example, U.S. Pat. No. 4,721,612, discloses a method and composition for the preparation of conventional lipid vesicles (liposomes) the bilayers of which comprise a salt form of an organic acid derivative of a sterol, such as the tris-salt form of a sterol hemisuccinate. The method disclosed therein allows for liposome formation which may be used to entrap compounds which are insoluble in aqueous solutions, such as bioactive agents of limited solubility. This conventionally formed liposome, however, includes no method for controlling delivery.

In contrast, liposomes of the present invention, because of their unique construction are highly sensitive to both pH and ionic strength of the surrounding medium in which they reside and are therefore specifically deliverable. This unique property results in part because they are formed of alkylammonium fatty acyl salts which are stabilized by a salt bridge. Such a characteristic provides the method to control the release of the load. Preferably, the liposomes of this invention are formed with molecules which consist of the following parts: a fatty acid of between 12 and 28 carbon atoms; an $N_n,N_n$-dimethyl-1,n-diamino alkyl (DDA) chain with the number of carbons (n) being equal to 2–8, for example $N_3,N_3$-dimethyl-propyl-1,3-diamine [$NH_2(CH_2)_3N(CH_3)_2$]; and a fatty acid of between 10 and 30 carbon atoms, together forming the ADDA. To form its basic structure, one molecule of fatty acid is linked via an amide bond to the primary amino group of the DDA to form an acyl-DDA (ADDA), for example, behenyl-DDA or palmitol-DDA. Such ADDA material is available under the tradename Catemol from the Phoenix Chemical Co. of Somerville, N.J., i.e., Catemol 220 and 160, respectively.

When the fatty acid is behenic acid ($C_{22}$) and the DDA has 3 carbon atoms, the molecule would be $N_1$-behenamido-$N_2$, $N_2$-dimethylpropyl-1,3-diamine [$CH_3(CH_2)_{20}CONHCH_2CH_2CH_2N(CH_3)_2$] (BDDP). Phoenix also sells another major group of chemicals which are a mixture of Catemol 220 and behenic acid, or Catemol 160 with palmitic acid to get Catemol 220B and 160P respectively. These are referred to herein as A-ADDAs (B-BDDP and P-PDDP). The ADDAs are cationic due to the quaternary amine; the A-ADDPs are inherently neutral. It should be noted that at pH less than about 10.5, the tertiary amine of the DDA will be protonated to form a quaternary amine with a positive charge. Free fatty acid carboxyl groups, attached to the tertiary amine group via the salt bridge, such as behenyl, have a pK of approximately 5 and so above a pH of 5 will be deprotonated and display a negative charge.

Figure 5:
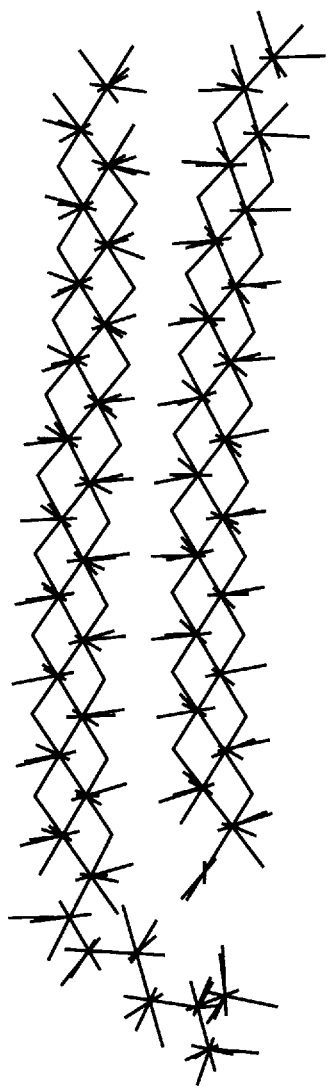
FIG. 5. Is an Energy Minimized Molecular Model of B-BDDP, produced by a molecular modeling program Insight II on a Silicon Graphics Indigo 4×24 work station.

To form A-ADDAS, the ADDA is mixed with a second fatty acid of between 12 and 28 carbon atoms in equimolar proportions and at a pH between 6 and 10 such that a salt is formed between the quaternary amine group of the ADDA and the carboxyl group of the fatty acid to form acyl ADDA (A-ADDA). An example where the ADDA is BDDP and the first fatty acid is behenic acid ($C_{22}$) would be behenyl-$N_1$-behenamido-$N_2,N_2$-dimethyl-propyl-1,3-diamine [$CH_3(CH_2)_{20}COO^- \cdot CH_3(CH_2)_{20}CONHCH_2CH_2CH_2NH^+(CH_3)_2$] (B-BDDP). An energy minimized molecular model of B-BDDP is presented in FIG. 5. It is apparent from the molecular model shown in FIG. 5 that these molecules are amphipathic: the salt bond region of the molecule being polar, the alkyl chain region of the molecule being hydrophobic. The molecule is also approximately cylindrical in cross-section and thus would be predicted to form bilayers and liposomes in aqueous media as described above.

The long chain (greater than twelve carbons) A-ADDA is dispersed in a suitable vehicle (water or any aqueous solution having a pH range between 4.5 and 10.5 and an ionic strength of less than, or equivalent to 1 molar NaCl) either by using a mechanical homogenizer at ambient temperature or by stirring at a temperature above that of the melting point of the components of the mixture. Following dispersion of the hydrocarbons in the vehicle, the mixture is subjected to high-sheer processing. The precise conditions for the high-sheer processing step must be established empirically for each mixture.

In this context, high-sheer processing refers to any technique which is capable of mixing ingredients (liquid, solid or mixtures of both) in such a manner that significant energy is imparted to the mixture. Examples would include sonnicators, high-speed mixers and microfluidizers, which are conventional. In particular, U.S. Pat. Nos. 4,533,254 and 4,908,154, disclose conventional methods and apparatus for forming emulsions, a term used to include microemulsions, which could be utilized herein. A sheet within an emulsion-forming liquid mixture is forced under pressure to impinge upon itself in a low-pressure turbulent zone of the liquid utilizing an apparatus comprising a plurality of nozzles with elongated orifices for ejecting, under pressure, sheets of the emulsion-forming liquid. The jets are arranged to effect impingement of the sheets along a common liquid jet interaction front, thereby imposing mechanical energy. Such devices offer great flexibility in choice and amounts of immiscible liquids and emulsifying agents.

Similarly, mixing ADDA with a long chain alcohol (C12, . . . C28), e.g., behenyl alcohol, will also result in a molecule with cylindrical cross-section. In this case, however, the cationic charge of the DDA is not neutralized and the liposomes which are formed have a large cationic surface charge.

EXAMPLE 1

B-BDDP is dispersed in phosphate-buffered saline (PBS: 20 mM phosphate buffer (pH 7.2) containing 140 mM NaCl) by stirring at a temperature of 70° C. for 20 minutes. The dispersion is then subjected to high-sheer processing by passage through a microfluidizer (Microfluidics, Newton, Mass.) five times, occurring at an operating pressure of 10,000 psi and an operating temperature between 10° C. and 20° C. It should be noted that any material(s) to be incorporated into the liposomes are added either at the initial mixing stage or immediately prior to high-shear processing.

Figure 6:
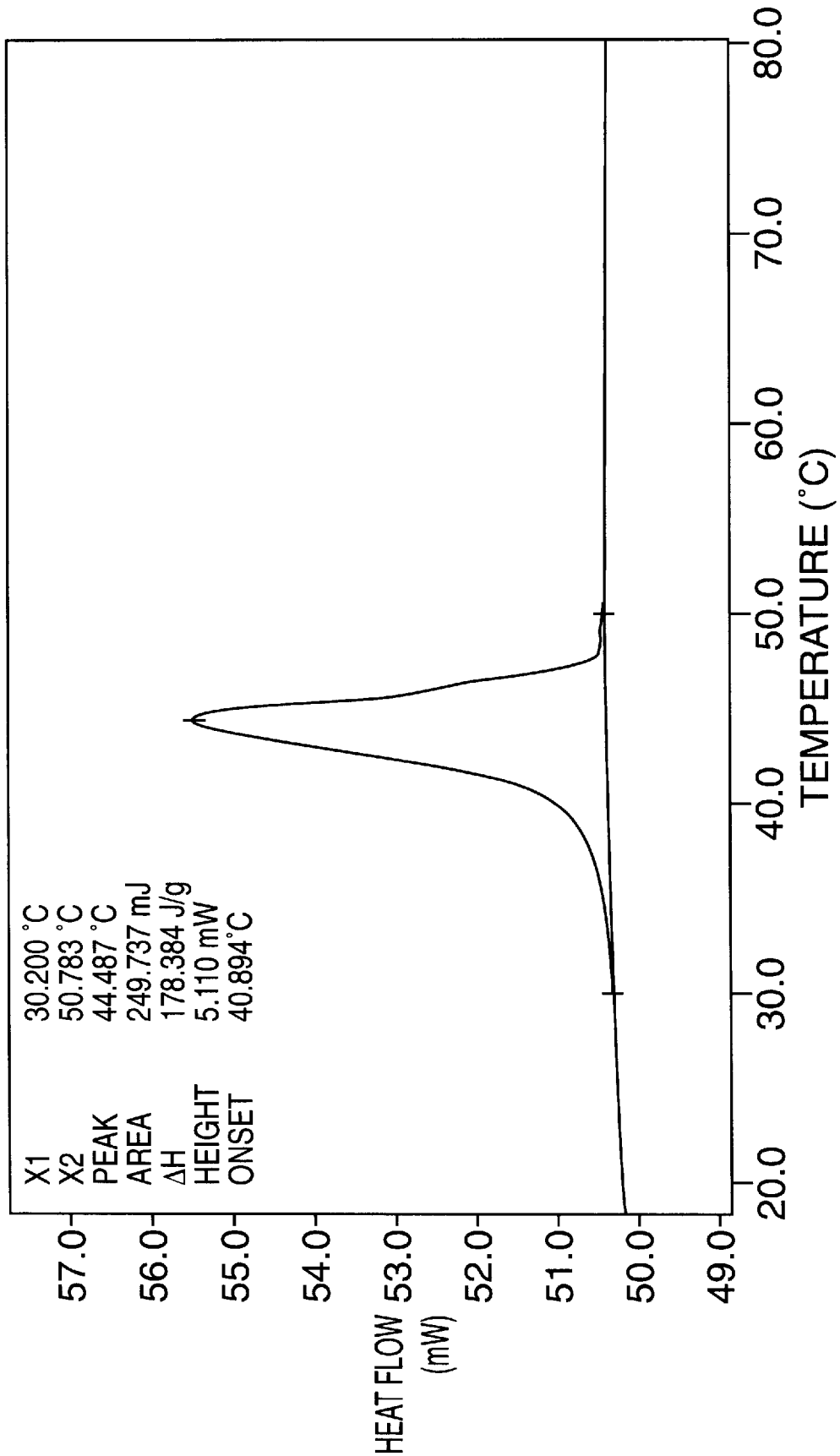
FIG. 6 is a differential scanning calorimetry plot (thermogram) of P-PDDP Liposomes prepared as described in the text.
Figure 7:
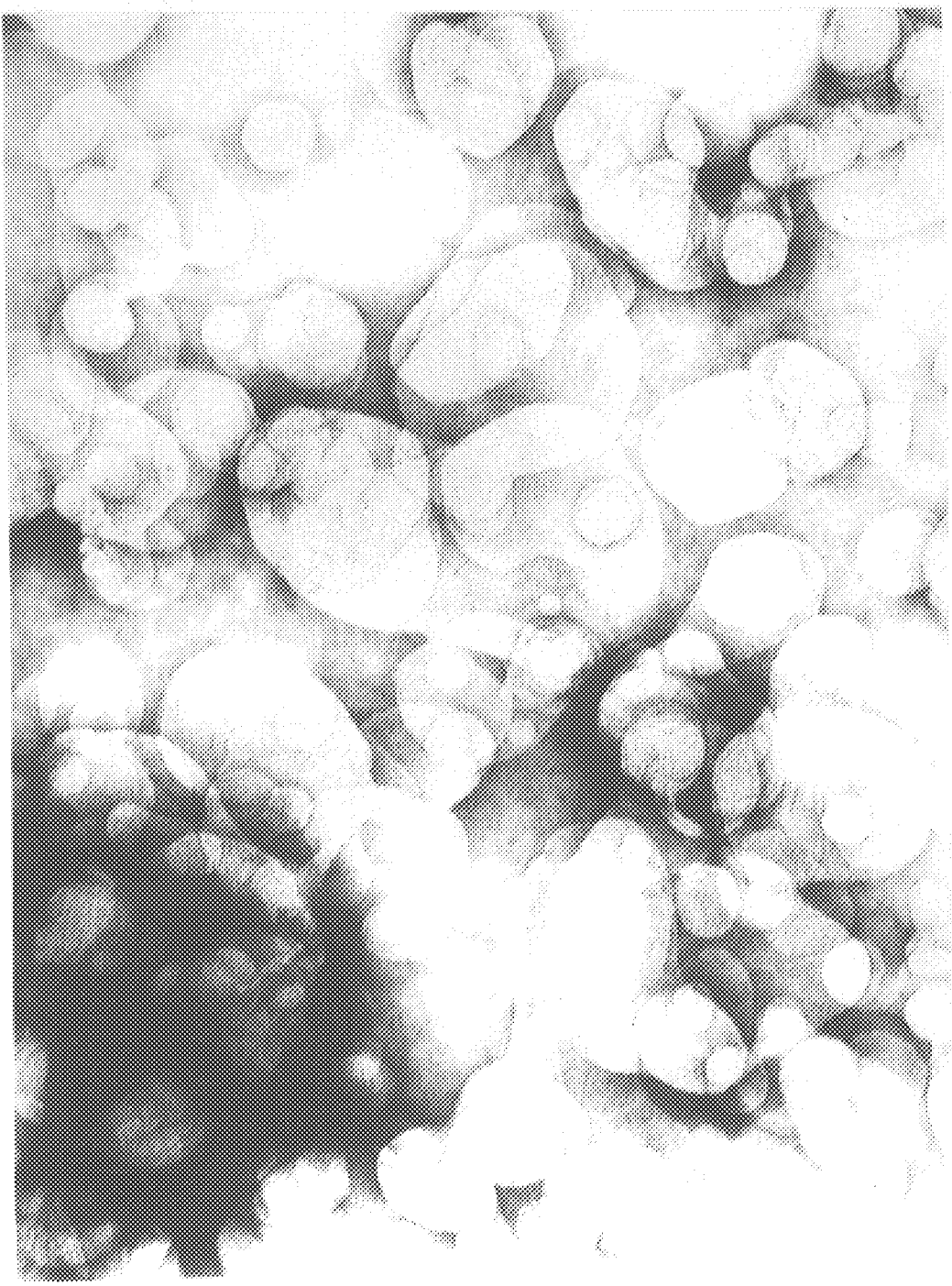
FIG. 7 is an image of a B-BDDP formed CATEZOMES™ liposomes, the image formed by negative stain electroscopy, in accordance with the invention.

The integrity of the liposomes formed in accordance with Example 1 was affirmed using differential scanning calorimetry. The presence of a transition temperature characteristic of molecules in a liquid crystal arrangement, such as the alkyl chains of the liposome membranes, is shown in FIG. 6. Further demonstration of the formation of liposomes by B-BDDP is shown in a representative electron micrograph of FIG. 7.

The testing utilized to determine the payload efficiency of the CATEZOMES™ liposomes formed according to Example 1 is described in Example 2. In Example 2, Glucose was chosen as a model substance to examine the encapsulation capabilities of the subject liposomes because it is a low-molecular weight (180 g/mole), water-soluble, non-charged molecule. These characteristics make for the most difficulty in encapsulation for the following reasons. The low molecular weight means that even small, transient imperfections in the lipid membrane would permit leakage of the glucose from the vesicular space to the extra-vesicular space and thus the glucose will rapidly leave any but the most perfect liposomes. The fact that glucose is entirely water-soluble, lipid-insoluble means that there is no chance of the glucose partitioning into the lipid phase and therefore no "false encapsulation" will be apparent. Since the ADDAs have a positive charge due to the amine group, a negatively charged molecule would tend to be attracted to the membranes. Again this would be apparent as false encapsulation. Thus, although glucose is very difficult to encapsulate in liposomes, it constitutes the perfect test material to prove the existence of stable, flawless, enclosed vesicles.

EXAMPLE 2

Glucose was added to a Catemol 220B/buffer dispersion at a concentration of 10% w/w and then the CATEZOMES™ liposomes were formed as described above in Example 1. Non-encapsulated, i.e., extra-vesicular, glucose was then removed by placing the liposomes into a dialysis bag (molecular weight cut-off 5,000 daltons), placing the dialysis bag into a beaker of PBS (phosphate-buffered saline) and then replacing the PBS with freshly made PBS every two hours for a twenty-four hour period. The concentration of glucose in the extravesicular volume (unencapsulated glucose) was measured by assaying the glucose in a liposome suspension in the presence or absence of 10% (v/v) Octoxynol-9 detergent, manufactured by Union Carbide Corporation, of Danbury, Conn. Octoxynol-9 is a non-ionic detergent which disrupts the liposomes and permits the equilibration of glucose between intra- and extra-vesicular spaces. An assay kit, purchased from Sigma Chemical Company of St. Louis, Mo. (product number 115), was used according to the manufacturer's instructions. This assay is based on the enzymatic conversion of glucose to glucose-6-phosphate with the concomitant reduction of nicotinamide dinucleotide phosphate (NADP) which can be detected spectrophotometrically. The absorption (520 nm) of the test sample is then extrapolated by comparison to a linear progression of standard (known) concentrations of glucose. Statistical analysis results of the slopes of these standard curves in the absence or presence of oetoxynol-9 is presented in Table I. These results assured that no interference from the detergent was apparent.

TABLE I

Statistical Analysis of Glucose Standard Curves.

| [Octoxynol-9] | 0% | 10% |
|---|---|---|
| n | 32 | 28 |
| Mean Slope | 0.249 | 0.262 |
| Standard Deviation | 0.020 | 0.036 |

The concentration of glucose in the intravesicular volume (encapsulated glucose) is then determined by subtraction of the extra-vesicular glucose (measured in the absence of octoxynol-9) from the total glucose (measured in the presence of octoxynol-9) (Equation 1).

$$[Glucose]_{inside} = [Glucose]_{total} - [Glucose]_{outside} \quad \text{Equation 1.}$$

In studies of liposomal encapsulation and stability, it is common to refer to "latency" which is the concentration of encapsulated payload expressed as a percentage of the total payload (Equation 2).

$$Latency = [Glucose]_{inside} \div [Glucose]_{total} \times 100 \quad \text{Equation 2.}$$

The concentration of intravesicular glucose is defined interchangeably herein, either in terms of concentration (mg/ml) or latency as defined above.

The encapsulation ability of liposomes made in accordance hereto, which are referred to interchangeably herein by their tradename CATEZOMES™ liposomes, from various A-ADDAs in various vehicles was also compared. All the CATEZOMES™ liposomes were formed in accordance with Example 1 above-described. For comparison, "standard" or conventional liposomes, i.e., those made from a phospholipid, 1,2-dipalmitoyl-sn-glycero-3-phosphocholine (DPPC), were also tested. The resulting data are summarized in Table II. It is clear that no matter the chain length, all of the A-ADDAs were shown to form sealed liposomes which encapsulated varying amounts of glucose. Furthermore, the process was clearly shown by the resulting data to be independent of the buffer system being used.

TABLE II

Glucose Encapsulation by Liposomes of Various Composition.
(Values are in [Glc]in, mg/ml)

| Buffer | B-BDDP | S-SDDP | P-PDDP | DPPC |
|---|---|---|---|---|
| Tris-Buffered Saline | 0.5 | 1.5 | ND | ND |
| Phosphate-Buffered Saline | 0.3 | 4.1 | 1.7 | 1.0 |
| Water | 0.3 | 3.9 | 1.9 | 1.0 |

B-BDDP, behenyl $N_1$-behenamido-$N_2,N_2$-dimethyl-propyl-1,3-diamine [$CH_3(CH_2)_{20}COO^-.CH_3(CH_2)_{20}CONHCH_2CH_2CH_2NH^+(CH_3)_2$]

TABLE II-continued

Glucose Encapsulation by Liposomes of Various Composition.
(Values are in [Glc]in, mg/ml)

| Buffer | B-BDDP | S-SDDP | P-PDDP | DPPC |
|---|---|---|---|---|

Figure 8:
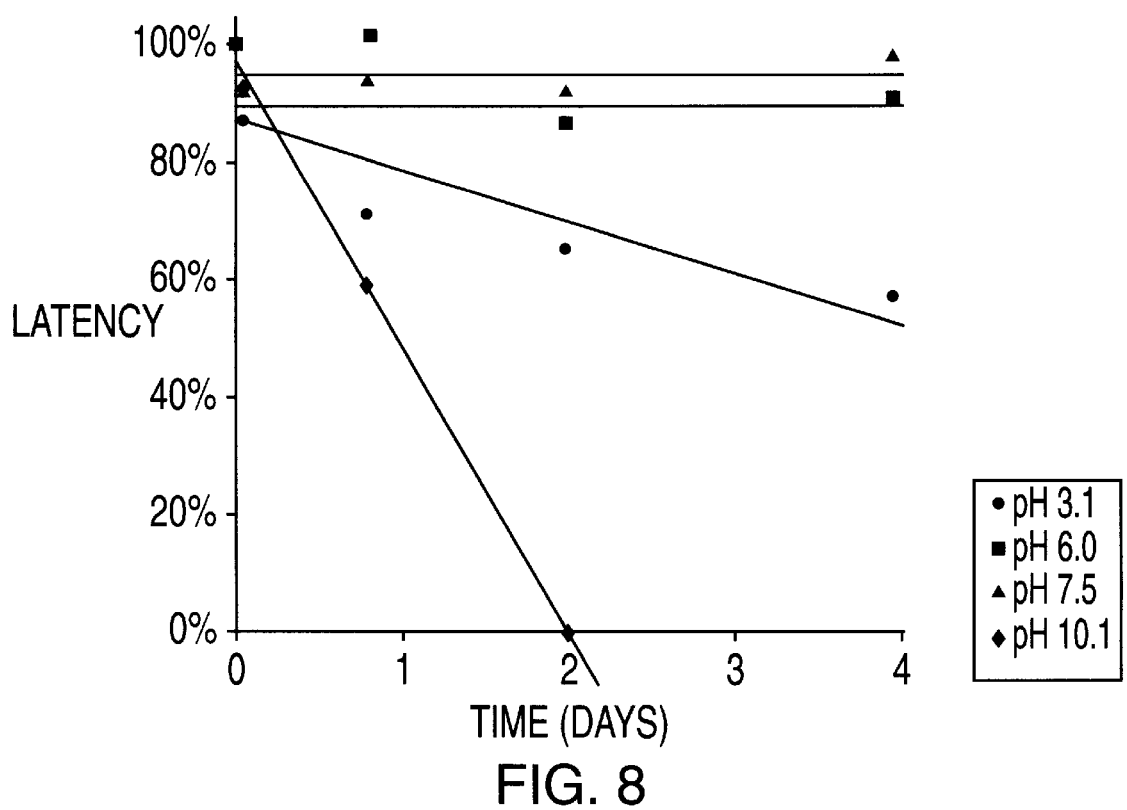
FIG. 8 is a plot of latency of a B-BDDP CATEZOMES™ liposomes formed in accordance herein.

S-SDDP, stearoyl $N_1$-stearoylamido-$N_2,N_2$-dimethyl-propyl-1,3-diamine [$CH_3(CH_2)_{16}COO^-.CH_3(CH_2)_{16}CONHCH_2CH_2CH_2NH^+(CH_3)_2$]
P-PDDP, palmitoyl $N_1$-palmitoylamido-$N_2,N_2$-dimethyl-propyl-1,3-diamine [$CH_3(CH_2)_{14}COO^-.CH_3(CH_2)_{14}CONHCH_2CH_2CH_2NH^+(CH_3)_2$]
DPPC, 1,2-dipalmitoyl-sn-glycero-3-phosphocholine; Tris-Buffered Saline, 20 mM Tris.HCl, pH 7.2, 140 mM NaCl; Phosphate-Buffered Saline, 20 mM phosphate, pH 7.2, 140 mM NaCl; ND - not determined As mentioned above, the molecular shape of the A-ADDAs, which precipitates bilayer and liposome formation, is in part dependent on the salt bridge comprising the molecule. Concomitantly, the stability of the liposomes is dependent upon changing pH and/or ionic strength, which acutely affects the salt bridge. FIG. 8 shows the latency over time of B-BDDP liposomes prepared in buffers of various pH but identical ionic strength. The B-BDDP liposomes containing glucose were prepared as described above (Example 1.) Samples of these liposomes were then placed into phosphate buffers of various pH as shown, but with constant ionic strength. The latency (Equation 2) of the liposomes was then measured, as described in the text, at various times following the onset of the experiment.

Figure 9:
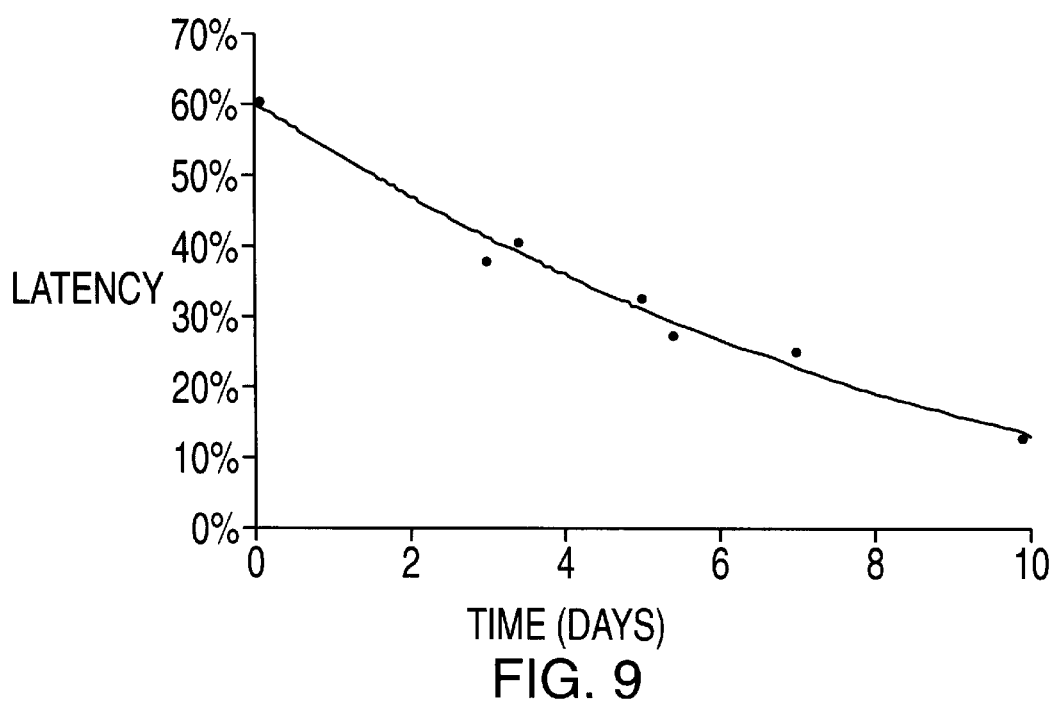
FIG. 9 is a plot of latency of a B-BDDP CATEZOMES™ liposomes containing glucose.

The measurement results clearly establish that the CATEZOMES™ liposomes are very stable at pH around neutrality, but become permeable to low molecular weight molecules such as glucose when the pH falls below 3 or increases above 10. This is entirely consistent with the notion that the salt bridge stabilizing the molecules is disruptable by pH. FIG. 9 shows the effect of increasing the ionic strength of the medium surrounding the CATEZOMES™ liposomes to 1.4M NaCl. Clearly, the increased ionic strength disrupts the molecular structure of the B-BDDP and causes the liposomes to become permeable.

The experiments presented for B-BDDP in FIG. 8 and FIG. 9 were repeated for several other A-ADDAs and the data are presented in Table III.

TABLE III

Effects of pH and Ionic Strength on the Half-Life of A-ADDA Liposomes.

| | pH 3 | pH 10 | pH 7 | Hypertonic |
|---|---|---|---|---|
| B-BDDP | <3 days | <1 day | >1 month | <1 day |
| S-SDDP | <1 day | <1 day | >1 month | <1 day |
| P-PDDP | <1 day | <3 days | >1 month | <1 day |
| DPPC | 3 days | >1 month | >1 year | >1 year |

B-BDDP, behenyl $N_1$-behenamido-$N_2,N_2$-dimethyl-propyl-1,3-diamine [$CH_3(CH_2)_{20}COO^-.CH_3(CH_2)_{20}CONHCH_2CH_2CH_2NH^+(CH_3)_2$]
S-SDDP, stearoyl $N_1$-stearoylamido-$N_2,N_2$-dimethyl-propyl-1,3-diamine [$CH_3(CH_2)_{16}COO^-.CH_3(CH_2)_{16}CONHCH_2CH_2CH_2NH^+(CH_3)_2$]
P-PDDP, palmitoyl $N_1$-palmitoylamido-$N_2,N_2$-dimethyl-propyl-1,3-diamine [$CH_3(CH_2)_{14}COO^-.CH_3(CH_2)_{14}CONHCH_2CH_2CH_2NH^+(CH_3)_2$]
DPPC, 1,2-dipalmitoyl-sn-glycero-3-phosphocholine

EXAMPLE 3

BDDP and a less than equimolar amount of Behenyl acid is dispersed in PBS along with lysozyme. The resulting CATEZOME™ was found to display a cationic nature, and upon testing, found to bind readily to hair shafts and chitin shells of nits (eggs of head lice). Once the CATEZOMES™ liposomes are bound, surface interactions realize environmental characteristic changes, e.g., the result of the excretion of salts and/or acids by the skin or hair which cause payload release to begin and the lysozyme contacts and destroys the egg shell. Similarly, CATEZOMES™ liposomes formed in accordance hereto as containers for silicones were found to readily adhere to hair shafts for conditioning delivery.

EXAMPLE 4

CATEZOMES™ liposomes of this invention were made with BDDP & behenyl alcohol. Such CATEZOMES™ liposomes were tested for their ability to facilitate transfection, i.e., the delivery of genetic material. In particular, due to their cationic nature, the CATEZOMES™ formed thereby were able to deliver the gene for β-galactocidase to cells in culture and to airway epithelial cells in vivo.

What has been described herein is merely descriptive of the preferred embodiment of this invention. It is not meant to limit the scope and spirit of the invention, which is only to be limited by the following claims drawn in accordance with U.S. Patent Law.

What is claimed is:

1. A method of preparing a lipid vesicle from alkylammonium fatty acid salts, such that the resulting vesicle is substantive to hair, tissue culture cells, epithelial cells and skin, comprising the steps of:

(a) dispersing long chain acyl Nn, Nn-dimethyl-1, n-diamino alkyl (A-ADDA) molecules in a buffering solution with a load material for delivery, to form a dispersion, said buffering solution having a pH within a range of between around 3.0 to around 10.0 and an ionic strength less than or equivalent to one molar NaCl; and (b) subjecting the dispersion to high shear processing whereby cationic lipid vesicles containing the load material are realized.

2. The method defined by claim 1, wherein said load material is added to said buffering solution before said A-ADDA is added.

3. The method defined by claim 1, wherein said load material is added to said buffering solution after said A-ADDA is added.

4. The method defined by claim 1, wherein said buffering solution utilized in said step of dispersing comprises $H_2O$ and said alkylammonium fatty acid salt is a trialkylammonium fatty acid salt.

5. The method defined by claim 1, wherein said step of dispersing comprises dispersing with a mechanical homogenizer.

6. The method defined by claim 1, wherein said step of dispersing comprises stirring said A-ADDA and buffering solution at a temperature above that of the melting point of said A-ADDA.

7. The method defined by claim 1, wherein said step of dispersing comprises preparing said buffering solution to have a pH in a range of between 5.5 and 10.5 and an ionic strength of less than the equivalent of 1 molar NaCl.

8. The method defined by claim 7, wherein the pH of said buffering solution is approximately 7.5.

9. The method defined by claim 1, wherein the step of dispersing comprises preparing said A-ADDA from a molecule of ADDA and a fatty acid at a pH of between 8 and 10.

10. The method defined by claim 9, wherein said step of dispersing comprises preparing behenyl-N-behenamido-N2, N2-dimethyl-propyl- 1,3-diamine (B-BDDP).

11. A lipid vesicle substantially comprised of alkylammonium fatty acid salts, wherein the resulting vesicle is substantive to hair, tissue culture cells, epithelial cells and skin, said vesicle formed by a process comprising the steps of:

(a) dispersing long chain acyl Nn, Nn-dimethyl-1, n-diamino alkyl (A-ADDA) molecules in a buffering solution to form a dispersion, said buffering solution having a pH within a range of between around 3.0 to around 10.0 and an ionic strength less than or equivalent to one molar NaCl; and (b) subjecting the dispersion to high shear processing whereby cationic lipid vesicles are formed.

12. The vesicle defined by claim 11, wherein said load material is added to said buffering solution before said A-ADDA is added.

13. The vesicle defined by claim 11, wherein said load material is added to said buffering solution after said A-ADDA is added.

14. The vesicle defined by claim 11, wherein said buffer solution utilized in said step of dispersing comprises $H_2O$ and the alkylammonium fatty acid salt is trialkylammonium fatty acid salt.

15. The vesicle defined by claim 11, wherein said step of dispersing comprises dispersing with a mechanical homogenizer.

16. The vesicle defined by claim 11, wherein said step of dispersing comprises stirring said A-ADDA and buffering solution at a temperature above that of the melting point of said A-ADDA.

17. The vesicle defined by claim 11, wherein said step of dispersing comprises preparing said buffering solution to have a pH in a range of between 5.5 and 10.5 and an ionic strength of less than the equivalent of 1 molar NaCl.

18. The vesicle defined by claim 17, wherein the pH of said buffering solution is approximately 7.5.

19. The vesicle defined by claim 18, wherein said preparing utilizes a fatty acid comprising behenic acid.

20. The vesicle defined by claim 18, wherein said step of dispersing comprises preparing behenyl-N-behenamido-N2, N2-dimethyl-propyl-1,3dramine (B-BDDP).

21. An in vivo delivery system for encapsulation and delivery of a material, which material is encapsulated within a lipid vesicle and deliverable upon the occurrence of a triggering condition comprising a change in pH or ionic strength, wherein said lipid vesicle structure substantially comprises an acyl $N_n,N_n$-dimethyl-1,n-diamino alkyl chain salt banded to a fatty acid (A-ADDA) such that a hydrophilic portion of said vesicle is cationic, whereby the resulting vesicle is substantive to hair, tissue culture cells, epithelial cells and skin to enhance the system's ability to deliver said material.

22. The delivery system defined by claim 21, wherein said cationic portion of said vesicle readily adheres to proteins.

23. A cationic lipid vesicle comprising a fatty acyl salt of a long chain amide, wherein the stability of said vesicle is controllable by controlling the stability of a salt bridge linking said fatty acyl and amide, such that the resulting vesicle is substantive to hair, tissue culture cells, epithelial cells, and skin.

24. The cationic lipid vesicle of claim 23, wherein said salt bridge is controlled by varying at least one of pH and ionic strength of a medium containing said vesicles.

25. The system defined by claim 21, wherein the material is selected from the group consisting of hydrophobic and hydrophilic materials.

* * * * *